United States Patent [19]
Villeneuve et al.

[11] Patent Number: 5,798,523
[45] Date of Patent: Aug. 25, 1998

[54] IRRADIATING APPARATUS USING A SCANNING LIGHT SOURCE FOR PHOTODYNAMIC TREATMENT

[75] Inventors: Luc Villeneuve, Montréal; Gérard Miller; Robert Bernier, both of Dorval; Claude Laurendeau, Boucherville, all of Canada; Prabir Kumar Pal, Calcutta, India

[73] Assignee: Theratechnologies Inc., Montreal, Canada

[21] Appl. No.: 685,598

[22] Filed: Jul. 19, 1996

[51] Int. Cl.$^6$ ............................ A61N 5/01; A61N 5/06
[52] U.S. Cl. .................. 250/234; 250/205; 250/492.1
[58] Field of Search ........................ 250/234, 235, 250/236, 205, 393, 390.03, 363.01, 363.02, 363.03, 363.09, 370.07, 492.1, 492.2, 492.23; 378/65

[56] References Cited

U.S. PATENT DOCUMENTS

| | | |
|---|---|---|
| Re. 31,370 | 9/1983 | Mashimo et al. |
| 3,902,971 | 9/1975 | Fletcher et al. ............ 195/103.5 R |
| 3,909,380 | 9/1975 | Day et al. .................... 204/180 R |
| 3,914,049 | 10/1975 | Basu et al. .......................... 355/68 |
| 4,052,620 | 10/1977 | Brunnett ....................... 250/445 T |
| 4,069,823 | 1/1978 | Isakov et al. ..................... 128/303.1 |
| 4,093,419 | 6/1978 | Tauber et al. ..................... 21/102 R |
| 4,230,129 | 10/1980 | Leveen ............................. 128/804 |
| 4,279,254 | 7/1981 | Boschetti et al. ................. 128/395 |
| 4,316,467 | 2/1982 | Muckerheide ................. 128/303.1 |
| 4,358,199 | 11/1982 | Isago ................................ 355/70 |
| 4,429,128 | 1/1984 | Thomas ........................ 250/214 R |
| 4,514,079 | 4/1985 | Okada et al. ......................... 355/8 |
| 4,671,256 | 6/1987 | Lemelson ......................... 128/1.1 |
| 4,749,867 | 6/1988 | Matsushita et al. ............. 250/442.1 |
| 4,864,359 | 9/1989 | Yamasaki et al. ................. 355/51 |
| 4,992,826 | 2/1991 | Nakabayashi ..................... 355/84 |
| 5,177,367 | 1/1993 | Suzuki ........................... 250/492.2 |
| 5,178,617 | 1/1993 | Kuisenga et al. .................... 606/17 |
| 5,288,647 | 2/1994 | Zimlich, Jr. et al. ............ 250/492.1 |
| 5,448,416 | 9/1995 | Okumura et al. .................. 359/727 |
| 5,452,720 | 9/1995 | Smith et al. .................... 128/653.1 |
| 5,464,013 | 11/1995 | Zemelson .......................... 378/65 |
| 5,491,329 | 2/1996 | Urakami et al. .................. 250/205 |

FOREIGN PATENT DOCUMENTS

| | | |
|---|---|---|
| 0 633 506 | 11/1995 | European Pat. Off. |
| 2590489 | 5/1987 | France |
| 87 17 182 U | 3/1988 | Germany |
| WO91/18646 | 12/1991 | WIPO |
| WO93/21842 | 11/1993 | WIPO |
| WO 95/12145 | 5/1995 | WIPO |
| WO97/19725 | 6/1997 | WIPO |

*Primary Examiner*—Edward P. Westin
*Assistant Examiner*—John R. Lee
*Attorney, Agent, or Firm*—Griffin, Butler, Whisenhunt & Szipl, LLP

[57] ABSTRACT

An apparatus for irradiating a biological substance with a substantially uniform quantity of radiation energy comprises a radiation-generating device for producing radiation energy, a support structure for receiving the biological substance, and a motorized mechanism for reciprocating the radiation-generating device along a given path whereby the biological substance receives radiation energy from the radiation-generating device at each passage of the radiation-generating device. A series of sensors lie into a given plane and are subjected to radiation energy from the radiation-generating device upon each passage of that radiation-generating device for sensing and measuring the quantity of radiation energy by surface unit passing through the given plane and reaching the biological substance. Finally the radiation-generating device and the motorized mechanism are de-energized when the measured quantity of radiation energy by surface unit has reached a predetermined value.

13 Claims, 9 Drawing Sheets

IRRADIATING APPARATUS USING A SCANNING LIGHT SOURCE FOR PHOTODYNAMIC TREATMENT

BACKGROUND OF THE INVENTION

1. Field of the Invention

The present invention relates to an apparatus and a method for irradiating a substance, in particular but not exclusively a biological substance with a substantially uniform quantity of radiation energy.

The irradiating apparatus and method is suitable, in particular but not exclusively, to conduct an ex-vivo photodynamic treatment for destroying malignant cells, and for research purposes in related fields or other fields such as:

photodynamic therapy (PDT);

purging;

autologous transplantation;

laser, xenon and incandescent sources; and treatment of leukemia with photodynamic therapy.

2. Brief Description of the Prior Art

Preferential uptake of photosensitive dye and cytotoxicity of photodynamic therapy against leukemia cells have been previously demonstrated (see for example Jamieson C. H. et al. (1990) Leuk. Res., 14: 209–219).

However, there is currently a lack of safe, cheap and reliable irradiating apparatuses to enable the in vitro photodestruction of malignant cells while leaving intact the normal but suppressed residual cellular population. The prior art irradiating apparatuses fail to provide the following desirable characteristics:

large surface of irradiation;

uniform light delivery;

real time monitoring of energy accumulated;

wavelength flexibility to accommodate any photosensitizer;

safety of use;

simplicity of use; and low cost of purchase and operation.

OBJECTS OF THE INVENTION

An object of the present invention is therefore to provide an apparatus and a method that eliminate the above discussed drawbacks of the prior art.

Another object of the present invention is to produce an irradiating apparatus endowed with the following characteristics:

large and variable surface of irradiation;

uniform light delivery (deviation≦5%);

real time monitoring of energy accumulated (Joules/cm$^2$);

wavelength flexibility to accommodate any photosensitizer;

programmable and automated procedures;

simplicity of use;

low cost of purchase and operation; and safe operation by personnel having a minimal technical formation.

SUMMARY OF THE INVENTION

More specifically, in accordance with the present invention, there is provided an apparatus for irradiating a biological substance with a substantially uniform quantity of radiation energy, comprising:

a radiation-generating device for producing radiation energy;

a motorized mechanism for reciprocating the radiation-generating device along a given path, the biological substance being placed along the given path at a given distance from the path to receive radiation energy from the radiation-generating device as the radiation-generating device reciprocates;

radiation sensor means lying into a given plane and subjected to radiation energy from the radiation-generating device upon each passage of the radiation-generating device for sensing and measuring the quantity of radiation energy by surface unit passing through the given plane and reaching the biological substance; and means for de-energizing the radiation-generating device and the motorized mechanism when the measured quantity of radiation energy by surface unit has reached a predetermined value.

The motorized reciprocating mechanism enables irradiation of a large surface with a uniform quantity of radiation energy, and the radiation sensor means and the de-energizing means enable automated irradiation of a substance with a predetermined quantity of radiation energy by surface unit (for example cm$^2$).

In accordance with preferred embodiments of the apparatus according to the invention:

the given path is a straight path, and the radiation-generating device is elongate and has a longitudinal axis generally perpendicular to this straight path;

the given plane is substantially parallel to both the straight path and the longitudinal axis of the elongate radiation-generating device;

the elongate radiation-generating device comprises at least one tube or is formed of two or three tubes and a reflector mounted on the side of the tubes opposite to the biological substance;

the radiation sensor means comprises a plurality of individual radiation sensors lying into the given plane, arranged into a series substantially parallel to the given path, and responsive to the radiation energy from the radiation-generating device at each passage of the radiation-generating device to produce respective output signals;

the motorized mechanism comprises means for moving the radiation-generating device along the given path in two opposite directions at constant speed; and the motorized mechanism comprises a variable speed motor, and further means are provided for pre-programming a speed of rotation of the variable speed motor.

Also in accordance with the present invention, there is provided a method for irradiating a biological substance with a substantially uniform quantity of radiation energy, comprising the steps of:

producing radiation energy by means of a radiation-generating device;

reciprocating the radiation-generating device along a given path;

placing the biological substance along the given path at a given distance from the path to receive radiation energy from the radiation-generating device as the radiation-generating device reciprocates;

sensing and measuring the quantity of radiation energy by surface unit passing through a given plane and reaching the biological substance; and de-energizing the radiation-generating device and stopping reciprocation of the radiation-generating device when the measured quantity of radiation energy by surface unit has reached a predetermined value.

Preferably, the step of sensing the quantity of radiation energy by surface unit comprises sensing radiation energy from the radiation-generating device upon each passage of the radiation-generating device through a plurality of individual radiation sensors lying into the given plane, arranging the radiation sensors into a series substantially parallel to the given path, wherein the radiation sensors are responsive to the radiation energy from the radiation-generating device at each passage of the radiation-generating device to produce respective output signals.

The step of measuring the quantity of radiation energy by surface unit advantageously comprises calculating the quantity of radiation energy by surface unit reaching the biological substance in response to the output signals from the radiation sensors.

The method of the present invention may further comprises the step of pre-programming the predetermined value.

According to one preferred embodiment, the reciprocating step comprises moving the radiation-generating device along the given path in two opposite directions at constant speed. Alternatively, the reciprocating step may comprise pre-programming a speed of reciprocation of the radiation-generating device.

The present invention further relates to an apparatus for irradiating a substance with a substantially uniform quantity of radiation energy, comprising:

- a radiation-generating device for producing radiation energy;
- a support structure for receiving the substance;
- a motorized mechanism for reciprocating one of the radiation-generating device and the support structure along a given path to produce a forth-and-back scanning movement of the radiation-generating device relative to the support structure whereby, at each scan, the substance receives radiation energy from the radiation-generating device;
- radiation sensor means lying into a given plane and subjected, at each scan, to radiation energy from the radiation-generating device for sensing and measuring the quantity of radiation energy by surface unit passing through the given plane and reaching the substance; and
- means for de-energizing the radiation-generating device and the motorized mechanism when the measured quantity of radiation energy by surface unit has reached a predetermined value.

The objects, advantages and other features of the present invention will become more apparent upon reading of the following non restrictive description of a preferred embodiment thereof, given by way of example only with reference to the accompanying drawings.

DETAILED DESCRIPTION OF THE PREFERRED EMBODIMENT

Figure 1:
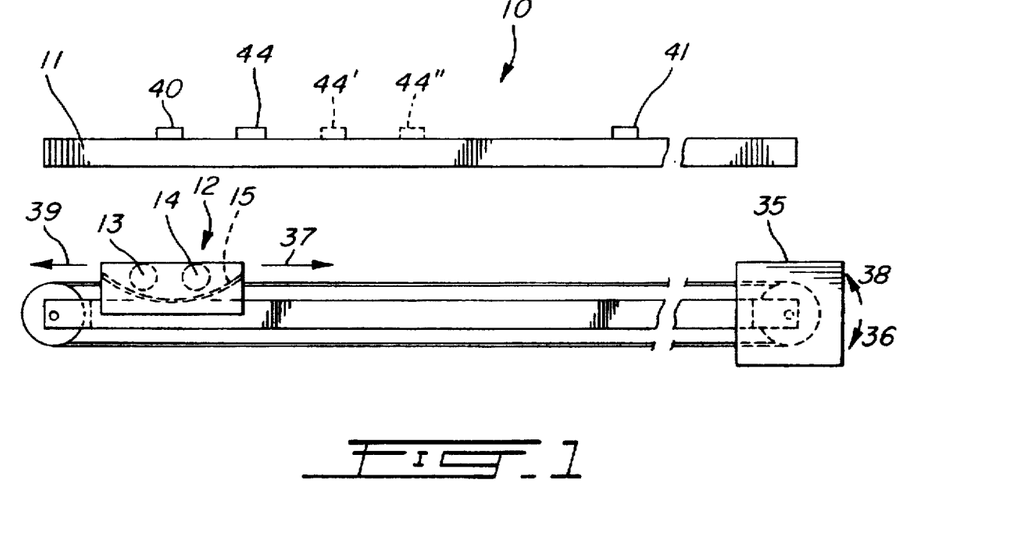
FIG. 1 is a side elevational view of an irradiating apparatus in accordance with the present invention.

The irradiating apparatus in accordance with the present invention is generally identified by the reference 10 in FIG. 1 of the accompanying drawings.

Referring to FIG. 1, the irradiating apparatus 10 comprises a substantially horizontal glass pane 11 on which the substance to be irradiated, in particular but not exclusively a biological substance in which malignant cells should be destroyed, is disposed. Under the glass pane 11 is mounted a light source 12.

Figure 2:
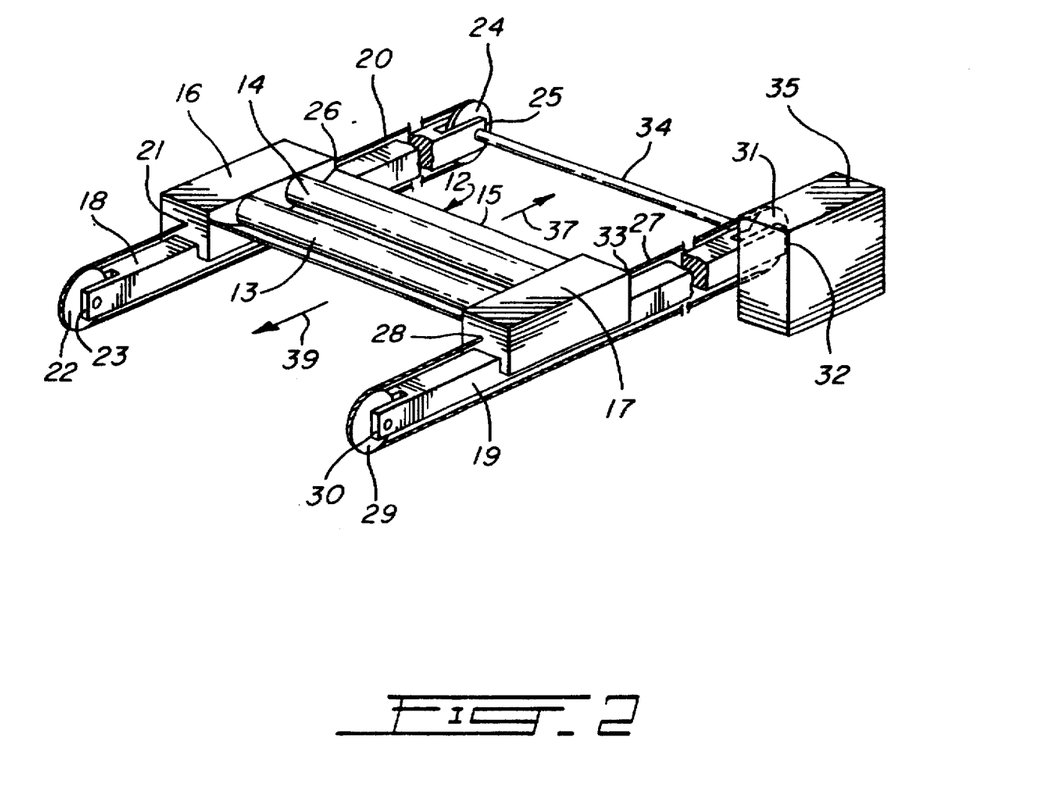
FIG. 2 is a perspective view of a motorized carriage mechanism forming part of the irradiating apparatus according to the invention.

In the example illustrated in FIGS. 1 and 2, a scanning light source 12 comprises two parallel, horizontally extending and mutually laterally adjacent tubes 13 and 14. An elongate reflector 15 generally parabolic in cross section is mounted under the laterally adjacent tubes 13 and 14. For example, tubes 13 and 14 are fluorescent tubes with appropriate phosphor coatings. In accordance with an alternative, the scanning light source 12 may comprise three parallel, horizontally extending and mutually laterally adjacent tubes. In accordance with another alternative embodiment, the fluorescent tubes are of the well known aperture type; the tube is partially coated to form a reflector, the coating leaving a transparent 30° window on the tube.

The two ends of the light source 12 are mounted on a motorized carriage mechanism. More specifically, the two ends of the light source 12 are mounted on respective sliding members 16 and 17 respectively sliding onto the guide rails 18 and 19.

A first steel wire 20 has one end 21 connected to a first end of the sliding member 16, passes around a pulley 22 situated at one end 23 of the guide rail 18 and around a pulley 24 located at the other end 25 of the guide rail 18, and has another end 26 connected to a second end of the sliding member 16. In the same manner, a second steel wire 27 has one end 28 connected to a first end of the sliding member 17, passes around a pulley 29 situated at one end 30 of the guide rail 19 and around a pulley 31 located at the other end 32 of the guide rail 19, and has another end 33 connected to a second end of the sliding member 17. The pulleys 24 and 31 are fixedly mounted onto a shaft 34 itself rotatable about its longitudinal axis by a reversible electric motor 35. Therefore, rotation of the reversible motor 35 in direction 36 (FIG. 1) will rotate the shaft 34 and the pulleys 24 and 31 in the same direction 36 to move the guide members 16 and 17 along with the light source 12 in direction 37 (FIGS. 1 and 2). In the same manner, rotation of the reversible motor 35 in direction 38 (FIG. 1) will rotate the shaft 34 and the pulleys 24 and 31 in the same direction 38 to move the guide members 16 and 17 along with the light source 12 in direction 39 (FIGS. 1 and 2).

Accordingly, appropriate control of the reversible electric motor 35 will cause reciprocation of the light source 12 successively in directions 37 and 39 along a linear path parallel to the glass pane 11 but perpendicular to the tubes 13 and 14 and the reflector 15.

Although a specific embodiment has been described and illustrated in the present disclosure, it should be kept in mind that other types of motorized scanning carriage can be used for constructing the irradiating apparatus according to the present invention. For example, reciprocating movement of the glass pane 11 supporting the substance to be irradiated can contemplated in the place of reciprocating movement of the light source 12.

Figure 3:
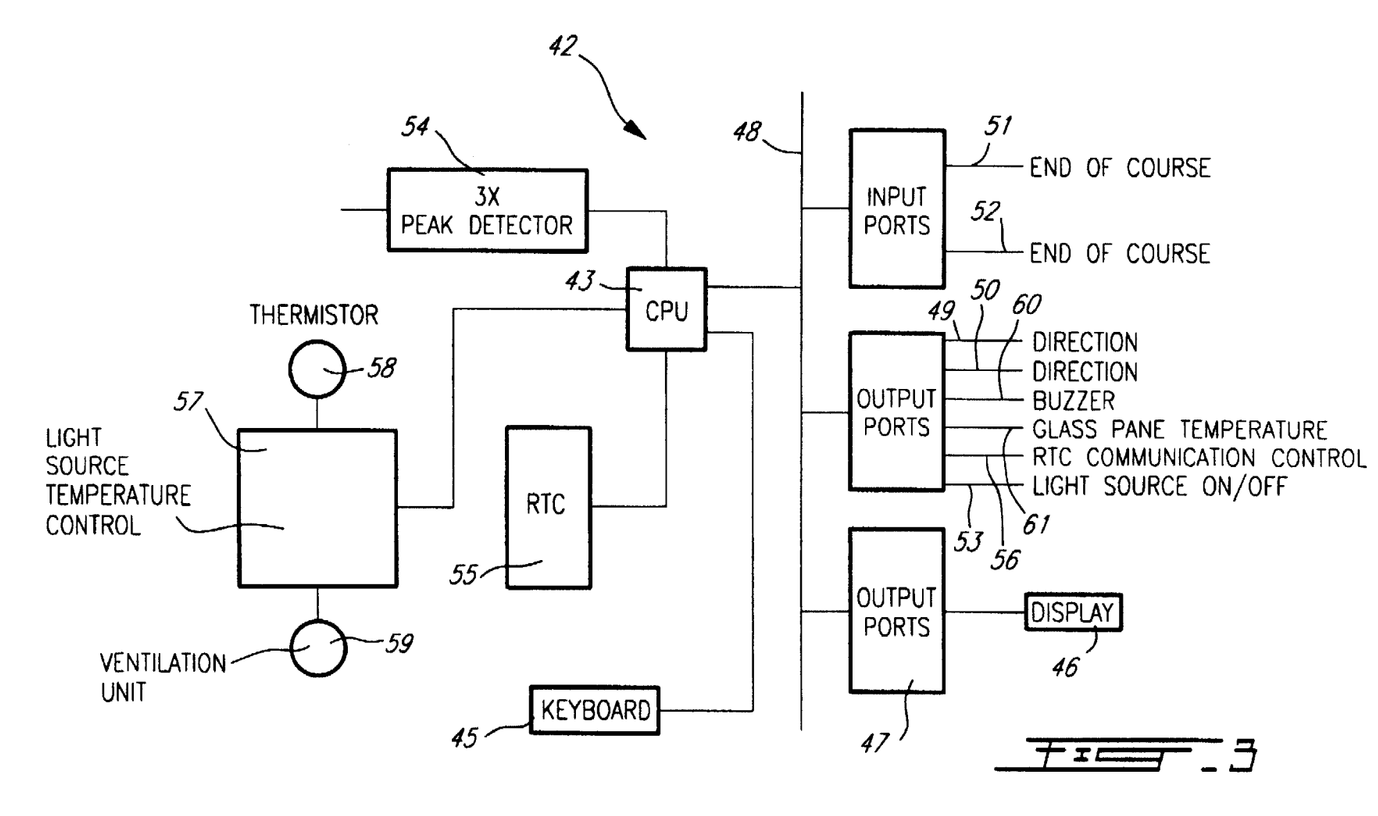
FIG. 3 is a block diagram of a control circuit forming part of the irradiation apparatus according to the present invention.

The irradiating apparatus 10 further comprises a control circuit 42 illustrated under the form of block diagram in FIG. 3 of the appended drawings. This control circuit 42 comprises a central processing unit (CPU) 43 which controls operation of the irradiating apparatus 10.

A keyboard 45 is connected to the central processing unit 43. A display 46 is also connected to the central processing unit 43 through output ports 47 and a data bus 48.

The keyboard 45 and display 46 will be used by the operator to calibrate the sensors (to be described hereinafter), to enter the parameters of a given treatment, and to start and stop the treatment as well as the operation of the irradiating apparatus 10.

After the parameters of a given treatment are entered and that treatment is started through the keyboard 45, the central processing unit 43 will control the operation of the motor 35 (FIGS. 1 and 2) to reciprocate the light source 12. More specifically, rotation of the motor 35 in direction 36 to move the light source 12 in direction 37 is controlled by the central processing unit 43 through the bus 48 and an output port 49, and rotation of the motor 35 in direction 38 is controlled by the central processing unit 43 through the bus 48 and an output port 50.

In a first step, the central processing unit 43 turns the light source 12 on through the bus 48 and an output port 53 on and searches for the start position of the light source 12. If the light source 12 is initially located at the end-of-course position shown in FIG. 1, the central processing unit 43 will first control the motor rotation through the output port 49 to rotate the reversible electric motor 35 in direction 36 at a constant speed and to move the light source 12 along the reciprocating path in direction 37. When the light source 12 reaches the end 25 and 32 of the guide rails 18 and 19, the light source 12 irradiates a light sensor 41 mounted to the top face of the glass pane 11. The central processing unit 43 then receives a corresponding end-of-course signal from the sensor 41 through an input port 51 and the bus 48. In response to the end-of-course signal from the input port 51, the central processing unit 43 will control the motor rotation through the output port 50 to rotate the reversible electric motor 35 in direction 38 at the same constant speed and to move the light source 12 along the reciprocating path in direction 39. When the light source 12 reaches the ends 23 and 30 of the guide rails 18 and 19, the light source 12 irradiates a light sensor 40 mounted to the top face of the glass pane 11. The central processing unit 43 then receives a corresponding end-of-course signal from the sensor 40 through an input port 52 and the bus 48. The central processing unit 43 then control the motor rotation through the output port 49 to rotate the reversible electric motor 35 in direction 36 and move the light source 12 in direction 37. And so on . . .

Of course, this is not a requirement that the different sensors 40, 41 and 44's be mounted to the top face of the glass pane 11. Other locations can be contemplated.

Those of ordinary skill in the art will appreciate that since the intensity of light emitted from the tubes 13 and 14 is substantially constant over the length thereof, reciprocation of the light source 12 at a constant speed will irradiate with a uniform quantity of radiation energy by surface unit a major portion of the plane defined by the glass pane 11. The quantity of radiation energy by surface unit ($J/cm^2$) to radiate from the light source is programmable through the keyboard 45 as a treatment parameter in the central processing unit 43 before starting operation of the irradiating apparatus 10. To measure the quantity of radiation energy by surface unit radiated from the reciprocating light source 12, at least one light sensor 44 (three light sensors 44, 44' and 44" arranged into a series substantially parallel to the reciprocating path being illustrated in FIG. 1) detects light emitted from the light source 12 at each passage of this light source 12 past the sensor(s) 44. Each sensor 44 produces an output signal supplied to the central processing unit 43 through a corresponding peak detector 54. The signal(s) from the sensor(s) 44 is analog and must be analog-to-digital converted by the central processing unit 43 before acquisition thereof, and is used by the central processing unit 43 to calculate the radiation energy by surface unit from the light source 12 at each scan (or passage). The central processing unit 43 integrates in real time the radiation energy to obtain the total radiation energy by surface unit. The time remaining for completing the treatment may also be calculated by the central processing unit and displayed onto the display 46. When the total energy by surface unit calculated by the central processing unit 43 reaches the programmed value, the light source 12 and the motor 35 are turned off through the output ports 49, 50 and 53 to terminate the treatment. This is not a requirement that the measure of the quantity of radiation energy by surface unit radiated from the reciprocating light source be measured in this fashion. Other sensing device and data processing can be contemplated.

Also, the central processing unit will activate an alarm (not shown) when the total energy by surface unit as calculated is fluctuating outside a pre-programmed range.

A start time (hours:minutes:seconds) may be programmed in the central processing unit through the keyboard 45 and display 46.

If the motor 35 is a variable speed reversible electric motor, the speed of movement (cm/sec) of the light source 12 in either direction 37 or 39 may also be programmed in the central processing unit 43 through the keyboard 45 and display 46 as a treatment parameter.

If additional end-of-course sensors are mounted to the top face of the glass pane 11, the scanning distance (cm) can also be programmed in the central processing unit 43 through the keyboard 45 and display 46 as a treatment parameter.

Moreover, activation of a standby mode at the end of the treatment may be programmed in the central processing unit 43.

The central processing unit 43 may further be programmed to produce a report that will include:

the total number of scans of the light source needed to reach the programmed value of radiation energy by surface unit;

the average of radiation energy output of each scan;

the start time; and the stop time.

The above report may also comprises a temperature report for each tube 13 and 14; the temperature of each tube 13 and 14 being measured by the circuit 57 (FIG. 3) as will be described hereinafter. A temperature sensor connected to the central processor unit 43 may also be provided for measuring the temperature of the glass pane 11 and to activate a ventilator (not shown) to cool the glass pane 11 through an output port 61. An alarm (not shown) may also be activated when the temperature of the glass pane 11 is situated outside of a pre-programmed range.

The central processing unit 43 has lines available to provide RS232 link capabilities. Also, it is supplied with a real time clock 55 associated to an output port 56 for providing a clock signal in view of controlling communication with the central processing unit.

An isolated circuit 57 (FIG. 3) will maintain the temperature of the tubes 13 and 14 of the light source 12 at about 37° C., by measuring the temperature of the tubes 13 and 14 through a thermistor 58 and controlling a tube-cooling ventilation unit 59 in relation to this measured temperature.

If the temperature measured through the thermistor 58 exceeds a certain predetermined level, circuit 57 will send to the central processing unit 43 a signal enabling that unit 43 to take action by turning one of the tubes 13 and 14 off or by stopping the treatment. The central processing unit 43 will then activate an alarm by energizing a buzzer through an output port 60.

Evaluation of cell viability

The K562 chronic myelogeneous leukemia cell line (Lozzio, B. B. and Lozzio, C. B. (1979) Cancer Res., 3(6)-363–370) was obtained from the American Type Culture Collection (ATCC, 12301 Parklawn Drive, Rockville, Md. 20852 USA) under the accession number F-10601 R243-CCL. Cultures were maintained at 370° C. in a humidified incubator with an atmosphere of 95% air and 5% $CO_2$. The culture media (IMAM (Iscove Modified Dulbeco Media) supplemented with 10% fetal bovine serum) were changed bi-weekly and the cells resuspended at a concentration of 100.000/ml. Cells were shown to be mycoplasma negative by routinely testing at 4 weeks interval.

Before each experiment, cell viability was assessed and twice the number of required viable cells were distributed in each 15 ml test tube. Cells were then incubated for 1 hour at 37° C., then washed twice in PBS (Phosphate Buffer Saline) and resuspended in the culture media. Photodynamic therapy was then applied to the cell culture, immediately or after an incubation period at 37° C. The cell cultures were kept at room temperature of 37° C. during the application of photodynamic activation.

Evaluation of the efficacy of a scanning fluorescent source 12

Figure 4A:
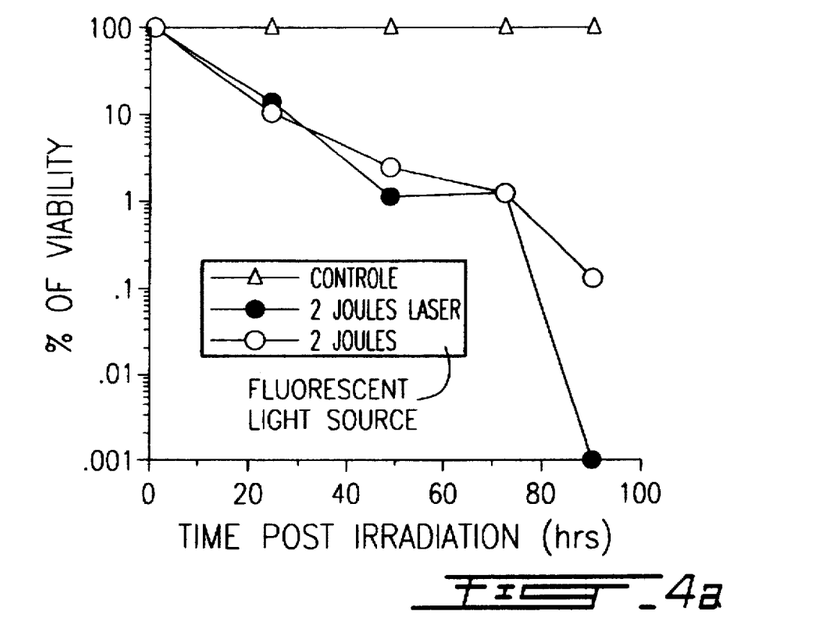
FIG. 4a is a graph comparing the tumoricidal effect of a fluorescent light source with the tumoricidal effect of a laser source at an energy level of 2 Joules/cm$^2$.
Figure 4B:
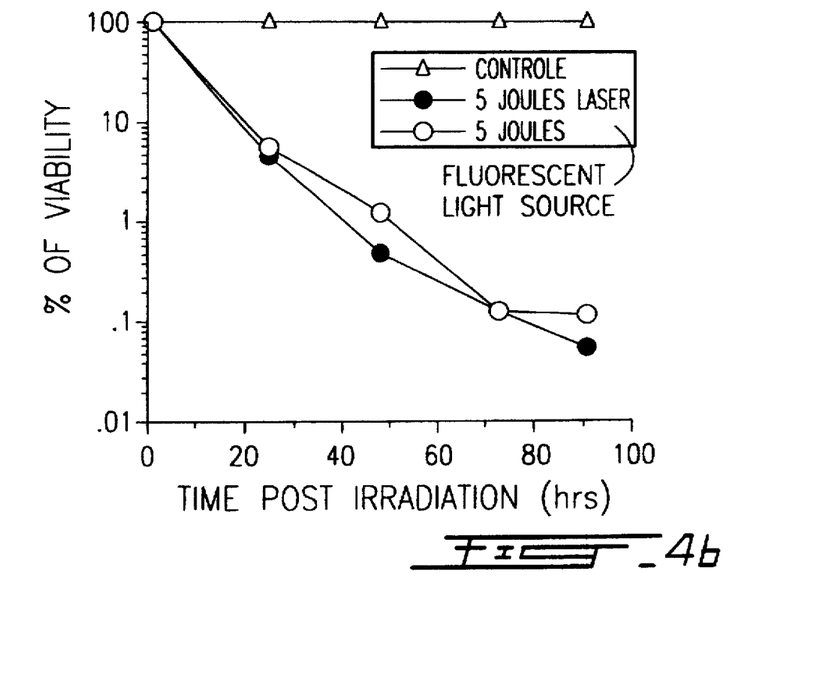
FIG. 4b is a graph comparing the tumoricidal effect of a fluorescent light source with the tumoricidal effect of a laser source at an energy level of 5 Joules/cm$^2$.

To assess the photo chemotherapeutic potential and the efficacy of the fluorescent light source 12, the leukemic K-562 cell line assay (as described above) was applied. Exposure to a 514 nm radiation from an argon ion laser at 2 and 5 $J/cm^2$ was used as a standard light source. The K562 cell line was exposed to 2 and 5 $J/cm^2$ after incubation with TH9402 photosensitizer for 20 minutes, a media change and 40 minutes extrusion time. FIGS. 4a and 4b essentially show that the radiation from a scanning fluorescent light source exerts a tumoricidal effect comparable to the standard laser source.

Phototoxitity against bone marrow cultures

It was observed that the photo treatment alone, using the laser or fluorescent light source, at energy levels up to 10 $Joules/cm^2$ did not affect neither the establishment of the long term culture nor the formation in semi solid assays of cellular colonies issued from the multiplication and differentiation of committed progenitors present in the bone marrow (colony forming unit 5-erythrocytes (CCU-E), blast forming unit-erythrocytes (BFU-E), colony forming units-granulocytes, macrophages, (CCU-G-M).

Conventional approaches for the treatment of cancer such as radiotherapy and intensive Chemotherapy are limited by their intrinsic toxicity and myelosuppressive effects. The introduction of allogenic and autologous bone marrow transplantation, have allowed the administration of marrow ablative chemotherapy and radiotherapy to patients whose malignancies cannot be cured with less aggressive measures. However, allogenic bone marrow transplantation is not widely accessible to patients because of the lack of suitable donors and the onset of graft-versus-host disease in recipients. To overcome these limitations and to expand the number of patents and age limit for intensive curative therapy, the potential benefit of in vitro bone marrow purging and autologous bone marrow transplantation has become widely acknowledged.

In an effort to develop a new irradiating apparatus that would allow safe, simple and reliable destruction of leukemic malignant cells, the present invention was developed and tested for the ex vivo photodynamic therapy of leukemia and metastatic cancers.

Figure 5A:
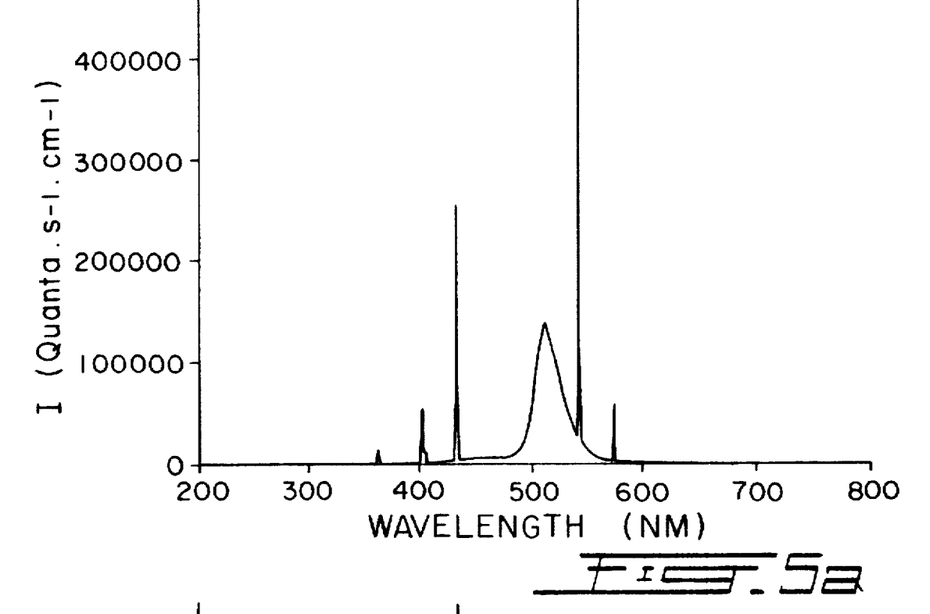
FIG. 5a is a graph showing the emission profile of a fluorescent tube with a filter.
Figure 5B:
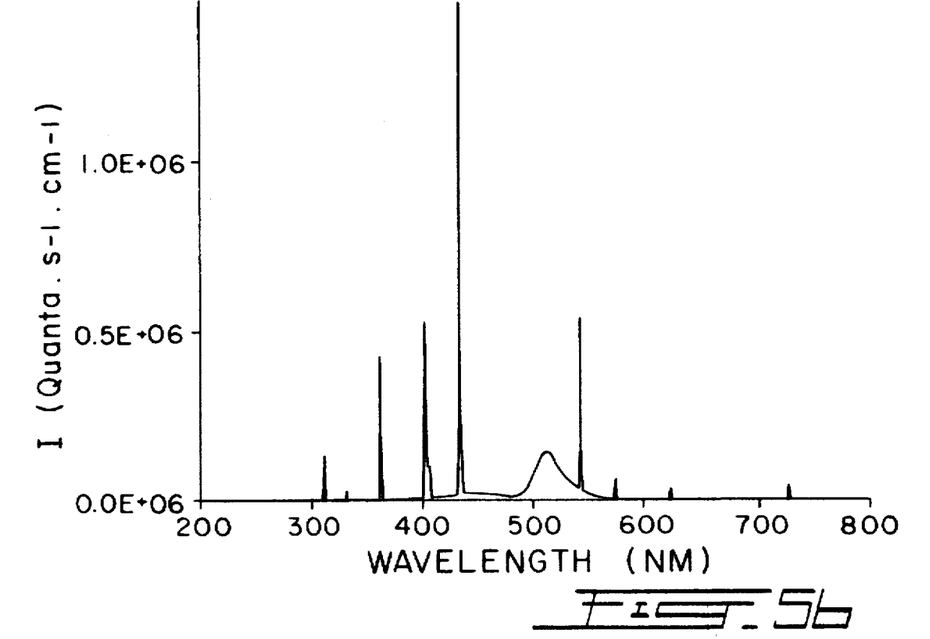
FIG. 5b is a graph showing the emission profile of the fluorescent tube without filter.

Characterization of the fluorescent tubes (i) The profile of a fluorescent tube with and without filter was measured. For that purpose, a fluorescence spectrophotometer (Model No. Spex Fluorolog-2), a fluorescent tube with a power supply, a scattering block and filters (LEE filters) were used. By placing the fluorescent tube in front of the window of the cell compartment and the scattering block in the cell holder the emission monochromator was scanned for 200 nm–800 nm, with or without a filter on the tube. The tube profiles with and without filter are shown in FIGS. 5a and 5b, respectively.

(ii) The special distribution of intensity, and the time dependence of light intensity at a particular location when the fluorescent tube is reciprocating were evaluated, and a table including the accumulated radiation energy versus the number of scans and the elapsed time was prepared.

A fluorescent tube (Model No. SR6064) with a power supply, filters (LEE filters), a powermeter (newport 818T-10), a centimeter scale and a timer (Fisher Scientific) were used.

A filter was installed on the fluorescent tube and the tube fitted into a tube housing. The fluorescent tube was powered and scanning (reciprocation) was carried out for 20 minutes in order to stabilize the power. After immobilizing the fluorescent tube, the centimeter scale was positioned at right angle with the fluorescent tube and fixed in position. The longitudinal axis of the tube was located at the 10 cm mark. Calibration of the permitter was verified and the power at each 0.5 cm along a line perpendicular to the tube was measured until the power measured was zero (on both sides of the lamp). After having placed the fluorescent tube in scanning mode, the timer was used to measure the time required for 40 scans both with lowest and highest scanning speed. Each distance of scanning was recorded. Also, the power distribution along the axis of the fluorescent tube was also measured.

Example

| Scan distance | Temps (sec)/40 scans | Speed cm/sec |
| --- | --- | --- |
| 18 | 13 | 55.38 |
| 28 | 18 | 62.22 |
| 40 | 24 | 66.66 |

In FIGS. 6–11, the detector area is 2.84 cm$^2$, the scanner speed is the lowest available speed ($\approx$55.38 cm/s), the fan (ventilator) is set to the minimum, and the tube temperature is 41° C.

Figure 6:
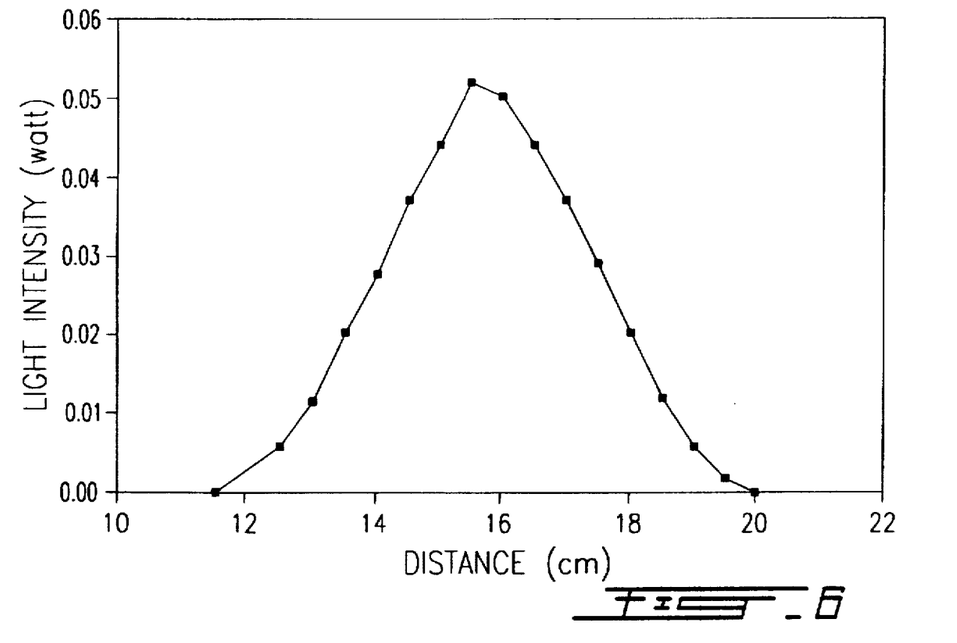
FIG. 6 is a graph showing the dependence of the light intensity of the static fluorescent tube to distance from the longitudinal axis of the tube, taking a 11.5 cm mark of a centimeter scale as origin.
Figure 7:
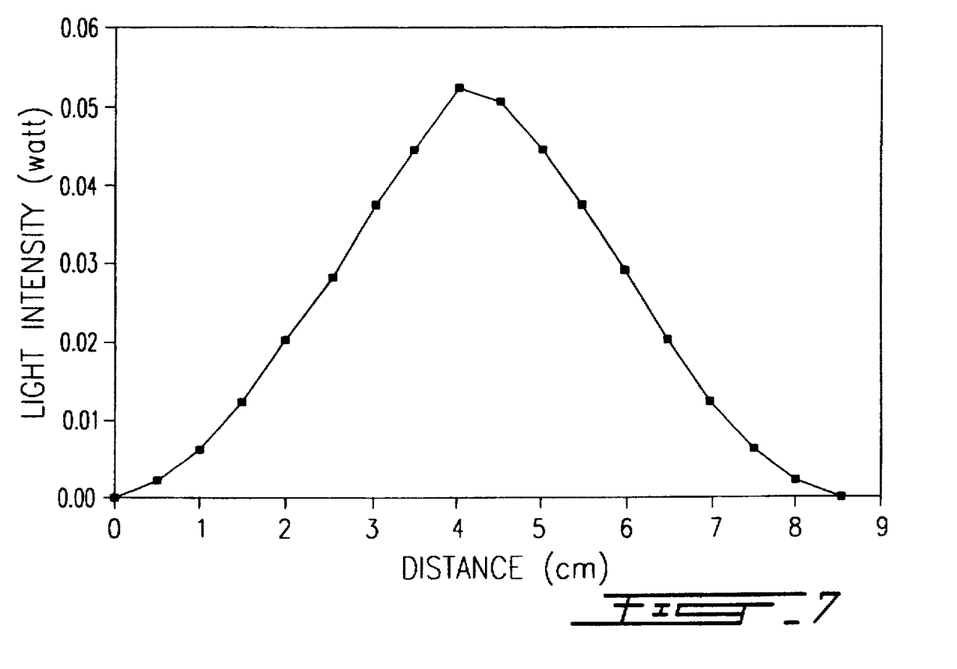
FIG. 7 is a graph showing the dependence of the light intensity of the fluorescent tube to distance from the longitudinal axis of the tube, taking 0 cm as the origin.
Figure 8:
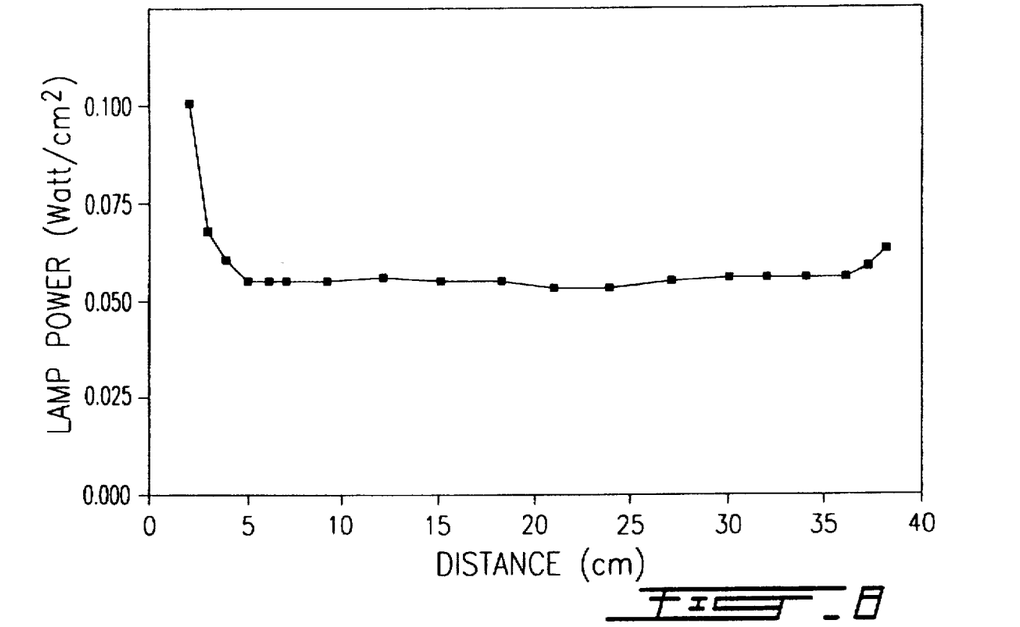
FIG. 8 is a graph showing the light intensity distribution along the length of the fluorescent tube.

FIG. 6 shows the dependence of the light intensity of a fluorescent tube to distance from the longitudinal axis of the tube, taking the 11.5 cm mark of the centimeter scale as origin. FIG. 7 shows the dependence of the light intensity of the same fluorescent tube to distance from the longitudinal axis of the tube, taking 0 cm as the origin. FIG. 8 shows the light intensity distribution along the length of the fluorescent tube.

Figure 9:
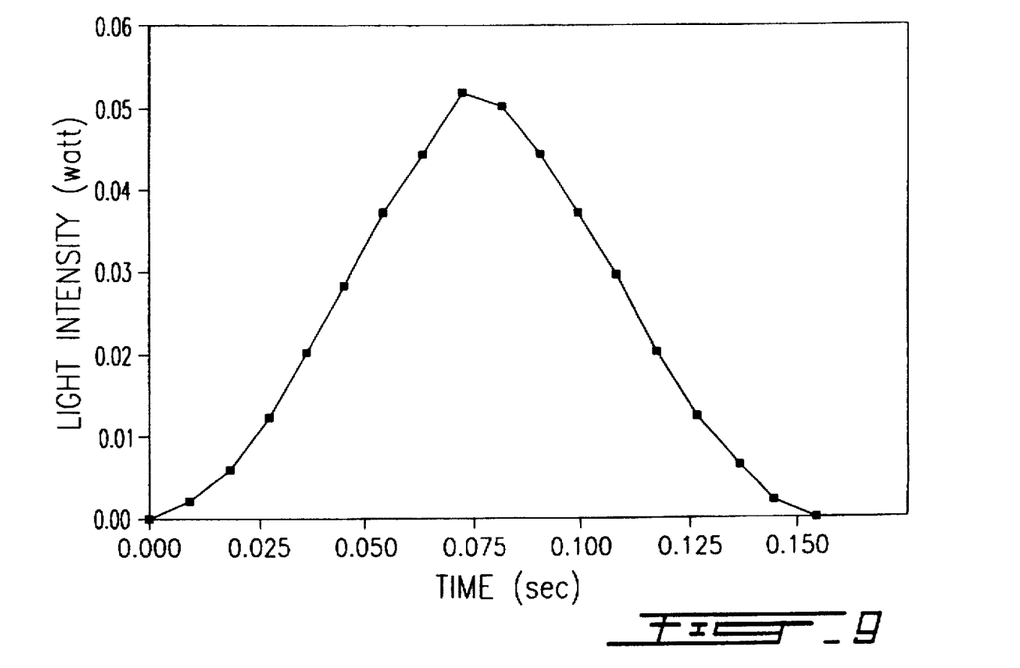
FIG. 9 is a graph showing the time dependence of the light intensity at a particular location when the tube is scanning (reciprocating) with a lowest speed and a shortest distance.
Figure 10:
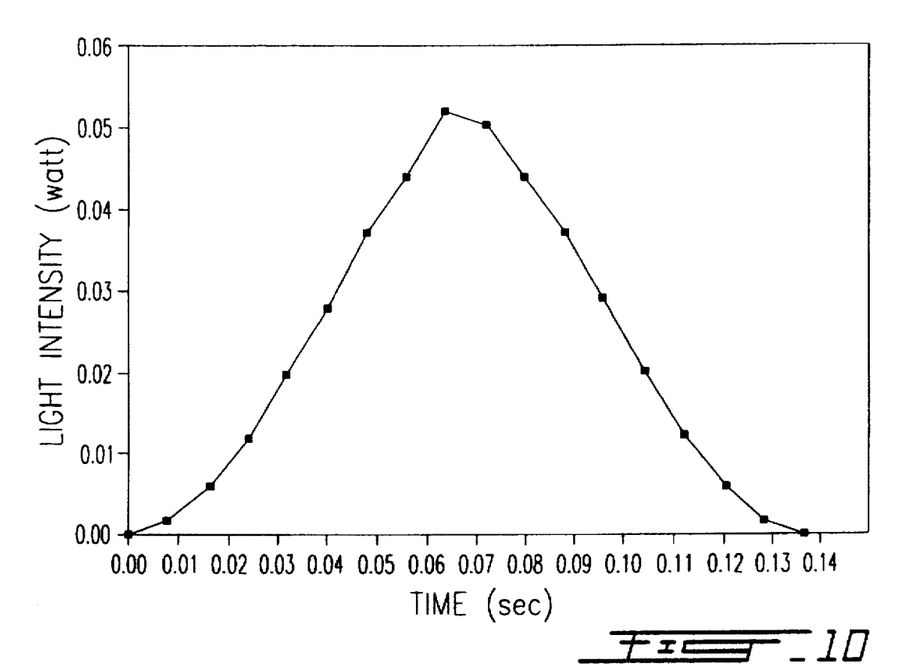
FIG. 10 is a graph showing the time dependence of the light intensity at a particular location when the fluorescent tube is scanning (reciprocating) with the lowest speed and an intermediate (central) distance.

To obtain the time dependence of the light intensity at a particular location when the fluorescent tube is scanning (reciprocating) at a particular speed, one has to convert the centimeter scale (x-scale) of FIGS. 1 and 2 to a time scale by dividing the distance with the corresponding speed. FIG. 9 shows the time dependence of the light intensity at a particular location when the tube is scanning (reciprocating) with the lowest speed ($\approx$55.38 cm/s) and the shortest scanning distance (18 cm). FIG. 10 shows the time dependence of the light intensity at a particular location when the fluorescent tube is scanning (reciprocating) with the lowest speed ($\approx$55.38 cm/s) and an intermediate scanning distance (28 cm). Finally, FIG. 11 shows the time dependence of the light intensity at a particular location when the fluorescent tube is scanning with the lowest speed ($\approx$55.38 cm/s) and the longest distance (40 cm).

To obtain the amount of energy per scan we have to integrate the area under the curve of FIG. 9 (for lowest speed of approximately 55.38 cm/s and scan distance of 18 cm. The quantity of radiation energy per scan is 0.00362 Joules per 2.84 cm$^2$ (0.001275 Joules/cm$^2$).

Similarly, for a scan distance of 28 cm, we have to integrate the area under the curve of FIG. 10 (for lowest speed). The quantity of radiation energy per scan is then 0.00322 Joules per 2.84 cm$^2$ (0.001135 Joules/cm$^2$).

Figure 11:
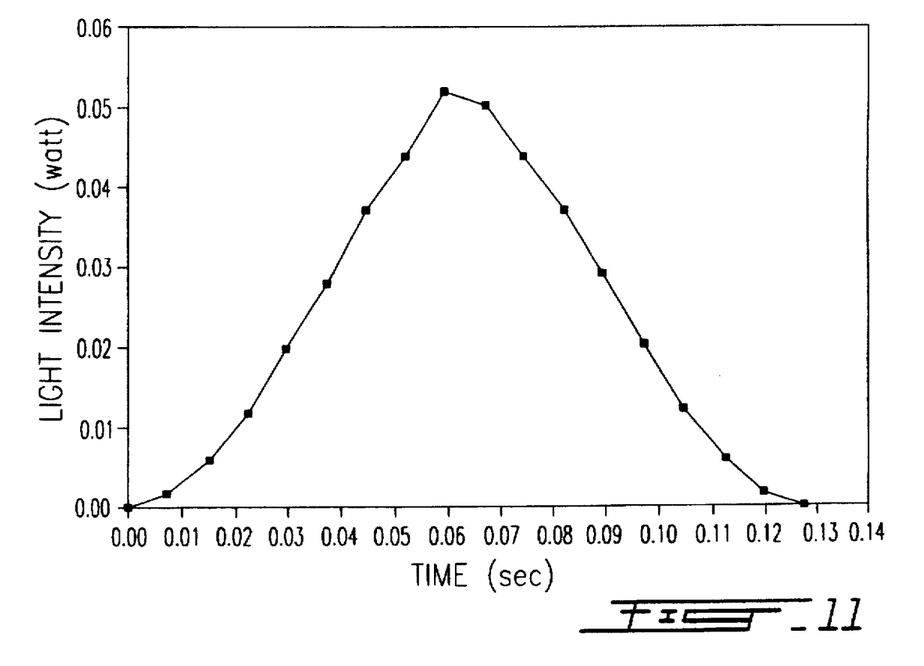
FIG. 11 is a graph showing the time dependence of the light intensity at a particular location when the fluorescent tube is scanning with the lowest speed and a longest distance.

Similarly, for a scan distance of 40 cm, we have to integrate the area under the curve of FIG. 11 (for lowest speed). The quantity of radiation energy per scan is 0.003008 Joules per 2.84 cm$^2$ (0.001059 Joules/cm$^2$).

Similar calculation is used by the central processing unit 43 to evaluate the radiation energy by surface unit at each scan, to obtain the total radiation energy by surface unit, to evaluate the number of scans required to reach a particular quantity of radiation energy (Joules/cm$^2$), to evaluate the time remaining to complete the treatment, that is the time required to reach the pre-programmed quantity of radiation energy by surface unit.

The present invention will be more readily understood by referring to the following examples which are given to illustrate the invention rather than to limit its scope.

EXAMPLE 1

Example 1 is a method of eradication of neoplastic cell line.

1. Diagnostic procedures

Cell viability assay (trypan blue exclusion) or limiting dilution assays (LDA) were used to monitor the presence of viable cells after treatment.

2. Cell culture

Cells cultures were maintained as recommended by the ATCC and incubated with the appropriate amount of photosensitizers prior to the application of the radiation (light).

3. In vitro purging

In vitro treatment consisted of short-term incubation of the cells with one or several of the selected photoactive compounds. Cells were maintained at 10,000,000 cells per ml and a concentrated stock solution of the dye was added to the media to reach the adequate dye concentration. The cells were incubated at 37° C. in the presence of the dye for periods of 20 to 40 minutes. Dye molecules still present in the media was removed by 2 cell washes with sterile dye free medium supplemented with 10% serum. Cells were then allowed an extrusion period in which a differential dye retention was created between normal and neoplastic cells. At the end of that period, cells were next exposed to radiant energy of sufficient intensities from a control laser source and the scanning fluorescent irradiating apparatus according to the present invention to effect photodynamic purging of neoplastic cells.

Efficacy of the photodynamic purging procedure was verified on an aliquot of the treated cell population.

4. Toxicity of TH9402 towards acute myeloid leukemia cell lines

Figure 12A:
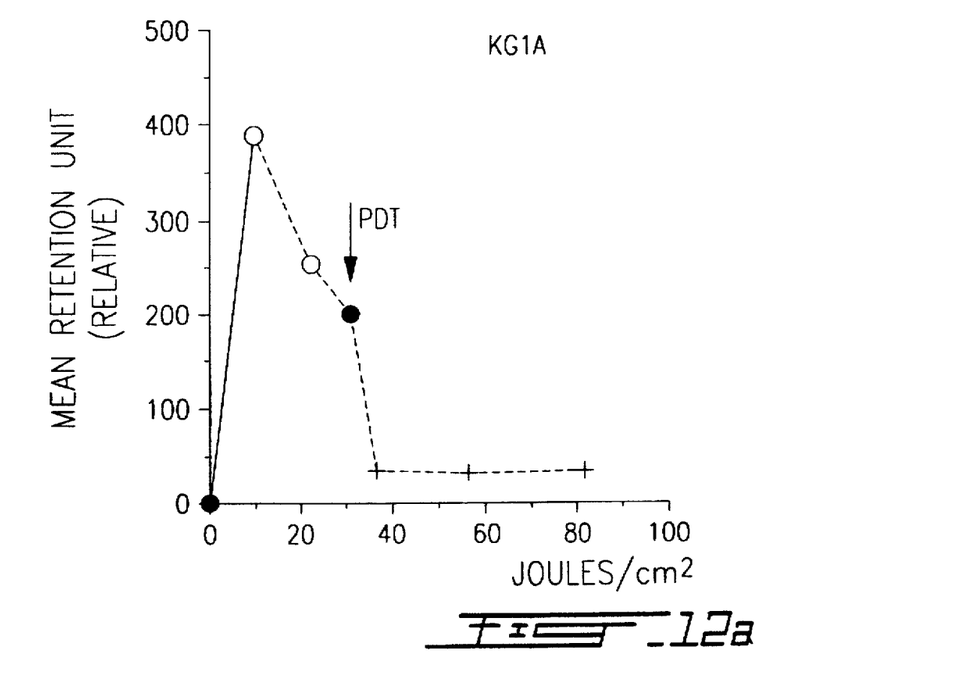
FIG. 12a is a graph depicting the retention profile of TH9402 in KG1A cell lines, during incubation with 10 µM of TH9402 followed by an extrusion period.
Figure 12B:
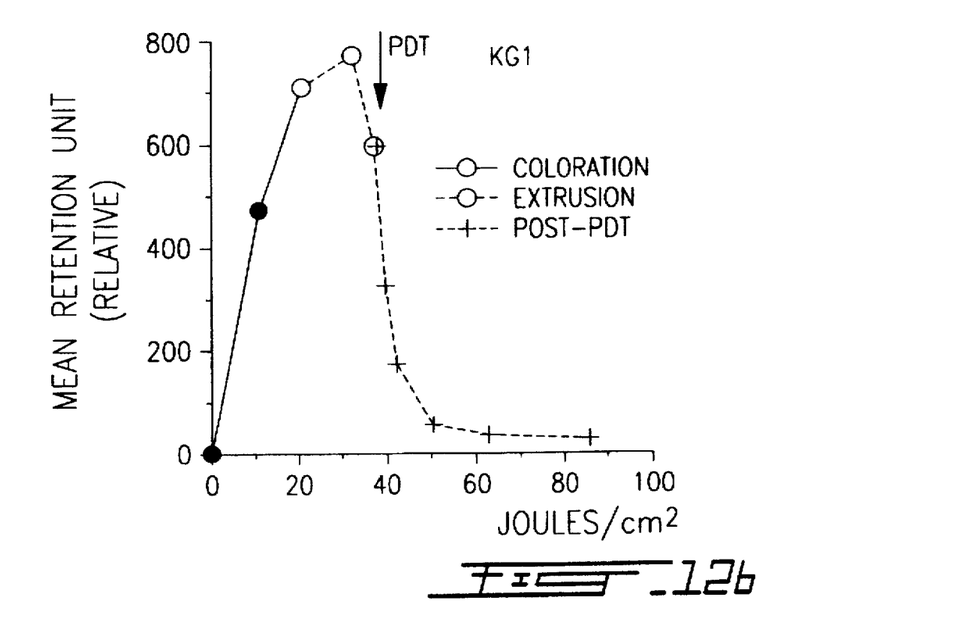
FIG. 12b is a graph depicting the retention profile of TH9402 in KG1 cell lines, during incubation with 25 µM of TH9402 followed by an extrusion period.
Figure 13A:
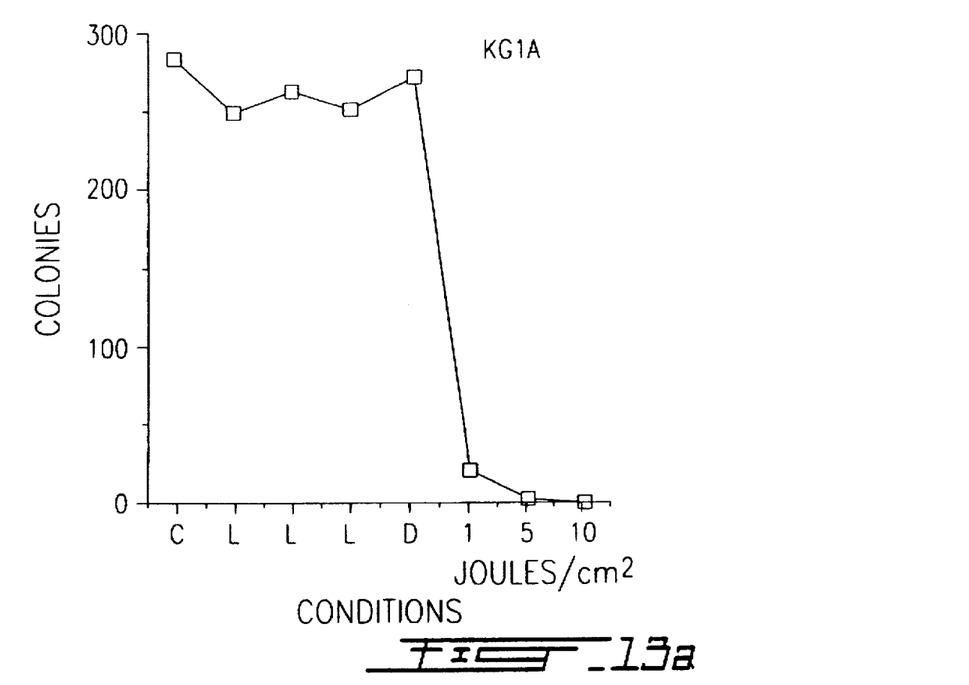
FIG. 13a is a graph showing cell colony count after various treatment: Nothing (N), light alone (L: 5 J/cm$^2$), dye alone (D) and photodynamic treatment (dye+light at 0.1, 0.5, 1, 2.5 and 5 J/cm$^2$)
Figure 13B:
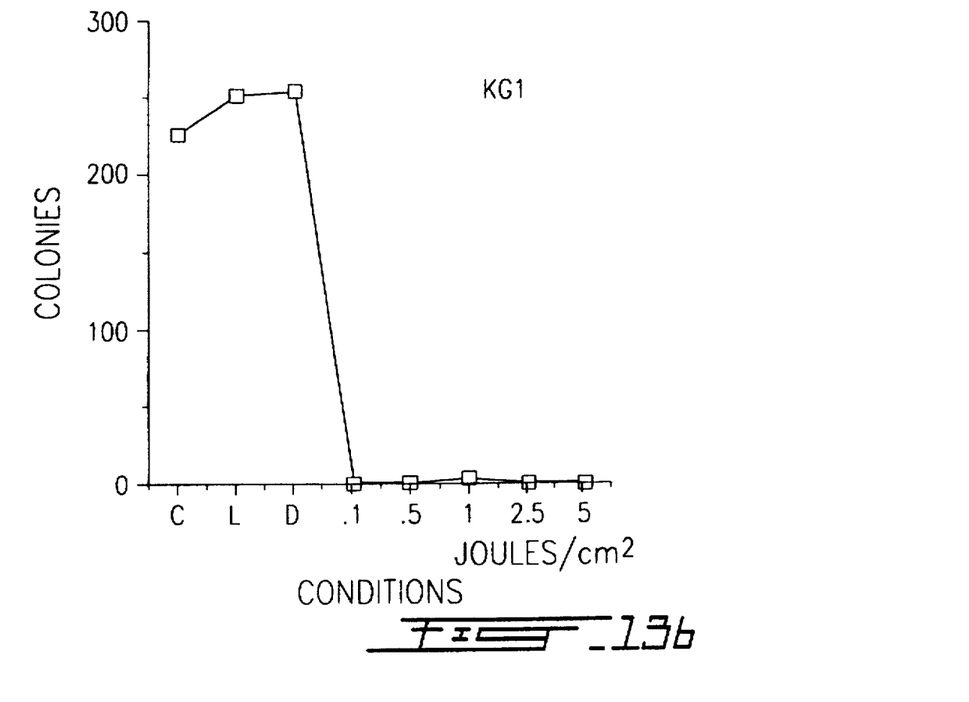
FIG. 13b is a graph showing cell colony count after various treatment: Nothing (N), light alone (L: 5 J/cm$^2$), dye alone (D) and photodynamic treatment (dye+light at 0.1, 0.5, 1, 2.5 and 5 J/cm$^2$).

FIGS. 12a and 12b depict the retention profile of TH9402 in KG1A and KG1 cell lines, respectively, during incubation with 10 or 25 µM respectively of TH9402 followed by an extrusion period. The arrow indicates the exact time at which PDT was applied on the cells. Retention units are relative to the unstained cells which have a background noise of about 3 units. FIGS. 13a and 13b show cell colony count after various treatment; Nothing (N), light alone (L: 5 J/cm$^2$), dye alone (D) and photodynamic treatment (dye+light at 0.1, 0.5, 1, 2.5 and 5 J/cm$^2$). In conclusion, PDT with 10 or 25 µM, respectively, of TH9402 completely eradicates KG1A and KG1 acute myeloid leukemia cell line.

EXAMPLE 2

Example 2 is a method of treatment of leukemias.

1. Diagnostic procedures

Diagnosis of chronic myelogenous leukemia (CML) was established using one or more of the following procedures on blood or bone marrow cells:

a) conventional cytogenetics studies with identification of Ph 1+methaphases harbouring the t(9:22); 10 b) fluorescent in situ hybridization for the detection of the bcr/abl rearrangement; and c) southern blot analysis for the detection of a rearranged bcr fragment or PCR-RT for the detection of chimeric bcr/abl messenger RNA.

2. Bone marrow harvesting

After diagnosis, bone marrow (BM) or peripheral blood (PB) derived hemopoietic stem cells were harvested using previously described procedures for the autologous marrow transplantation in cancer therapy (reviewed by Herzig G), (1991) Prog. Hematol., 12:1). Hemopoietic stem cells collected for autograft were immediately treated ex vivo as described below.

3. In vitro purging of leukemia

Ex vivo treatment consisted of short-term incubation of BM or PB stem cells with one or several of the selected photoactive compounds. Duration of incubation, cell concentration and drug molarity were determined for each patient using an aliquot of the harvested cell population. Excess of dyes was removed by cell washes with sterile dye free medium supplemented with 2% autologous serum. Cells were next exposed to radiant energy of sufficient intensities to effect photodynamic purging of leukemia cells.

Efficacy of the photodynamic purging procedure was verified on an aliquot of the treated cell population, before cryopreservation and/or re-infusion to the patient is performed. Until re-infusion to the patient, the cells will be cryopreserved in 10% dimethyl sulfoxyde (DMS))—90% autologous serum medium, at −196° C. in the vapour phase of liquid nitrogen.

4. Efficacy of TH9402 PDT towards chronic myeloid leukemia cells.

To demonstrate the feasibility of the approach for the treatment of CML patients, we treated fresh CML marrow from patients under previous treatment protocols and clinical status for their sensitivity to R1BR2 PDT and monitored their content of pH⁻ clonogenic precursors, throughout the treatment. Essentially, cells were exposed to 10 µM R1BR2 followed a dye extrusion period of 90 to 120 minutes and subsequent PDT (1 J/cm$^2$). Initial results indicate that R1Br2/PDT-mediated the eradication of the bcr/abl positive cells. Before treatment, plucked colonies from semi-solid assays scored over 90% positive for bcr/abl message while more than 95% of colonies tested negative after treatment (BFU-E, CCU-GM, CCU-Mix). Our results indicate that treatment conditions can be selected that selectively abrogate leukemia cells while leaving intact normal marrow progenitors in amounts deemed sufficient to successfully engraft a recipient. As shown in the following table, similar treatment conditions lead to 1) A 4-log reduction in the number of K 562 cells;

2) the innocuousness of the treatment on normal marrow clonogenic cells; and 3) the selective eradication of Ph-1 positive leukemic clonogenic cells as measured by the disappearance of the BCR-ABL message using the sensitive RT-PCR assay.

| Efficacy of photodynamic treatment using TH9402 to eradicate CML cells | | | | |
|---|---|---|---|---|
| | Colonies (% of control) | | Log reduction | Positivity PCR |
| Treatment | Untreated | PDT | PDT | PDT |
| Normal marrow | 100 | 42 | NA | 0 |
| K562 line | 100 | <0.001 | 4.81 | NA |
| CML Marrow | 100 | <1 to 4.5 | NA | 0 |

The above two (2) examples confirm the efficacy of the irradiating apparatus and method in accordance with the present invention.

Although the preferred embodiment of the present invention has been described in relation to the use of fluorescent tubes, it should be kept in mind that the present invention is not limited to the use of fluorescent tubes but includes the use of any other suitable radiation-generating device including lamps, tubes, etc.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An apparatus for homogeneously irradiating cells contained in a living biological substance, comprising:

a radiation-generating device for producing a substantially constant radiation along a given axis;

a motorized mechanism for reciprocating at generally constant speed the radiation-generating device along a given path angularly spaced apart from said given axis, the living biological substance being placed along the given path to receive radiation energy from the radiation-generating device as said radiation-generating device reciprocates;

stationary radiation sensor means exposed to radiation energy from the reciprocating radiation-generating device upon each passage of said reciprocating radiation-generating device for sensing and measuring the quantity of radiation energy reaching the living biological substance; and means for de-energizing the radiation-generating device and the motorized mechanism when the measured quantity of radiation energy has reached a predetermined value.

2. An apparatus as recited in claim 1, wherein said given path is a straight path, and wherein said straight path is generally perpendicular to said given axis.

3. An apparatus as recited in claim 1, in which the radiation-generating device comprises at least one tube generally parallel to said given axis.

4. An apparatus as recited in claim 1, wherein said radiation sensor means comprises a plurality of individual radiation sensors arranged into a series substantially parallel to said given path, and responsive to the radiation energy from the reciprocating radiation-generating device at each passage of said reciprocating radiation-generating device to produce respective output signals.

5. An apparatus as recited in claim 4, wherein said radiation sensor means further comprises a computer means responsive to the output signals from the radiation sensors to calculate the quantity of radiation energy reaching the living biological substance.

6. An apparatus as recited in claim 1, further comprising means for pre-programming said predetermined value.

7. An apparatus as recited in claim 1, wherein said motorized mechanism comprises a variable speed motor, and wherein said apparatus further comprises means for pre-programming a speed of rotation of said variable speed motor to thereby pre-program the generally constant speed of reciprocation of the radiation-generating device.

8. A method for homogeneously irradiating cells contained in a living biological substance, comprising the steps of:

producing a substantially constant radiation along a given axis by means of a radiation-generating device;

reciprocating the radiation-generating device at substantially constant speed along a given path angularly spaced apart from said given axis;

placing the biological substance along the given path to receive radiation energy from the radiation-generating device as said radiation-generating device reciprocates;

installing stationary radiation sensor means exposed to radiation energy from the reciprocating radiation-generating device upon each passage of said reciprocating radiation-generating device;

by means of the stationary radiation sensor means, sensing and measuring the quantity of radiation energy reaching the living biological substance; and de-energizing the radiation-generating device and stopping reciprocation of said radiation-generating device when the measured quantity of radiation energy has reached a predetermined value.

9. A method as recited in claim 8, wherein:

the step of installing static radiation sensor means comprises installing a plurality of individual radiation sensors arranged into a series substantially parallel to said given path; and the step of sensing the quantity of radiation energy comprises sensing radiation energy from the radiation-generating device upon each passage of said radiation-generating device through the plurality of individual radiation sensors, said radiation sensors being responsive to the radiation energy from the radiation-generating device at each passage of said radiation-generating device to produce respective output signals.

10. A method as recited in claim 9, wherein the step of measuring the quantity of radiation energy comprises calculating said quantity of radiation energy reaching the biological substance in response to the output signals from the radiation sensors.

11. A method as recited in claim 8, further comprising the step of pre-programming said predetermined value.

12. A method as recited in claim 8, wherein said reciprocating step comprises pre-programming a speed of reciprocation of the radiation-generating device.

13. An apparatus for homogeneously irradiating cells contained in a living biological substance, comprising:

a radiation-generating device for producing a substantially constant radiation along a given axis;

a support structure for receiving said living biological substance;

a motorized mechanism for reciprocating at generally constant speed one of said radiation-generating device and said support structure along a given path angularly spaced apart from said given axis, to produce a forth-and-back scanning movement of the radiation-generating device relative to said support structure whereby, at each scan, said living biological substance receives radiation energy from the radiation-generating device;

radiation sensor means exposed, at each scan, to radiation energy from the radiation-generating device for sensing and measuring the quantity of radiation energy reaching said living biological substance; and means for de-energizing the radiation-generating device and the motorized mechanism when the measured quantity of radiation energy has reached a predetermined value.

\* \* \* \* \*

UNITED STATES PATENT AND TRADEMARK OFFICE
CERTIFICATE OF CORRECTION

PATENT NO. : 5,798,523
DATED : August 25, 1998
INVENTOR(S) : Luc VILLENEUVE, et al.

It is certified that error appears in the above-indentified patent and that said Letters Patent is hereby corrected as shown below:

Column 6, line 28, change "control" to --controls--.
Column 9, line 65, change "distance of 18 cm." to --distance of 18 cm).--.

Signed and Sealed this

Thirtieth Day of March, 1999

Attest:

Q. TODD DICKINSON

*Attesting Officer*  Acting Commissioner of Patents and Trademarks